(12) United States Patent
Freedman et al.

(10) Patent No.: US 11,794,959 B2
(45) Date of Patent: Oct. 24, 2023

(54) CONTAINER AND LID WITH MULTIPLE SEALS THEREBETWEEN AND METHODS FOR MAKING AND USING THE SAME

(71) Applicant: CSP Technologies, Inc., Auburn, AL (US)

(72) Inventors: Jonathan R. Freedman, Auburn, AL (US); Donald Lee Huber, Auburn, AL (US); Brian Tifft, Auburn, AL (US); Franklin Lee Lucas, Jr., Opelika, AL (US)

(73) Assignee: CSP Technologies, Inc., Auburn, AL (US)

( * ) Notice: Subject to any disclaimer, the term of this patent is extended or adjusted under 35 U.S.C. 154(b) by 0 days.

(21) Appl. No.: 17/454,649

(22) Filed: Nov. 12, 2021

(65) Prior Publication Data
US 2022/0355983 A1    Nov. 10, 2022

Related U.S. Application Data

(63) Continuation of application No. 16/834,176, filed on Mar. 30, 2020, now Pat. No. 11,192,698, which is a
(Continued)

(51) Int. Cl.
*B65D 43/16* (2006.01)
*G01N 33/487* (2006.01)
(Continued)

(52) U.S. Cl.
CPC .......... *B65D 43/162* (2013.01); *A61B 50/30* (2016.02); *B65D 53/02* (2013.01);
(Continued)

(58) Field of Classification Search
CPC ........ B65D 2543/00564; B65D 43/162; B65D 53/02; B65D 2543/00092;
(Continued)

(56) References Cited

U.S. PATENT DOCUMENTS

| 1,192,135 A | 7/1916 | Stone |
| 2,733,829 A | 2/1956 | Lewitt |

(Continued)

FOREIGN PATENT DOCUMENTS

| CN | 102026890 A | 4/2011 |
| CN | 102795392 A | 11/2012 |

(Continued)

OTHER PUBLICATIONS

International Search Report issued in PCT/US2017/021010, dated Apr. 20, 2017.

*Primary Examiner* — Kareen K Thomas
(74) *Attorney, Agent, or Firm* — Mark T. Vogelbacker; Eckert Seamans Cherin & Mellott, LLC

(57) ABSTRACT

A moisture tight container includes a container body and a lid preferably linked to the body by a hinge. The body and lid include at least a first seal and a second seal in series to provide a moisture tight seal between the body and the lid. The first seal includes mating of thermoplastic-to-thermoplastic sealing surfaces of the body and lid respectively. The second seal includes mating of thermoplastic-to-elastomeric sealing surfaces of the body and lid, respectively, or of the lid and body, respectively.

21 Claims, 10 Drawing Sheets

Related U.S. Application Data continuation of application No. 16/081,597, filed as application No. PCT/US2017/021010 on Mar. 6, 2017, now Pat. No. 10,669,079.

(60) Provisional application No. 62/419,275, filed on Nov. 8, 2016, provisional application No. 62/303,483, filed on Mar. 4, 2016.

(51) Int. Cl.
*A61B 50/30* (2016.01)
*B65D 53/02* (2006.01)
*A61B 50/00* (2016.01)

(52) U.S. Cl.
CPC ............ *G01N 33/48778* (2013.01); *A61B 2050/0052* (2016.02); *A61B 2050/0056* (2016.02); *A61B 2050/0066* (2016.02); *A61B 2050/3014* (2016.02); *B65D 2543/0074* (2013.01); *B65D 2543/00092* (2013.01); *B65D 2543/00296* (2013.01); *B65D 2543/00527* (2013.01); *B65D 2543/00537* (2013.01); *B65D 2543/00629* (2013.01); *B65D 2543/00685* (2013.01); *B65D 2543/00796* (2013.01); *B65D 2543/00972* (2013.01)

(58) Field of Classification Search
CPC ........... B65D 2543/00296; B65D 2543/00527; B65D 2543/00537; B65D 2543/00629; B65D 2543/00685; B65D 2543/0074; B65D 2543/00796; B65D 2543/00972; A61B 50/30; A61B 2050/0052; A61B 2050/0056; A61B 2050/0066; A61B 2050/3014; G01N 33/48778
See application file for complete search history.

(56) References Cited

U.S. PATENT DOCUMENTS

| | | | |
|---|---|---|---|
| 3,275,180 A | 9/1966 | Optner | |
| 3,323,671 A | 6/1967 | Minarik, Jr. et al. | |
| 3,415,405 A | 12/1968 | Rausing et al. | |
| 3,419,179 A | 12/1968 | Fritz | |
| 3,441,161 A | 4/1969 | Baarn | |
| 3,593,909 A | 7/1971 | Bergmann | |
| 3,891,118 A | 6/1975 | Laurizio | |
| 4,022,352 A | 5/1977 | Pehr | |
| 4,061,226 A | 12/1977 | Essen | |
| 4,089,432 A | 5/1978 | Crankshaw et al. | |
| 4,132,225 A | 1/1979 | Whattam | |
| 4,291,818 A | 9/1981 | Nozawa et al. | |
| 4,403,712 A | 9/1983 | Wiesinger | |
| 4,457,458 A | 7/1984 | Heinol | |
| 4,545,508 A | 10/1985 | Cribb, Jr. et al. | |
| 4,718,571 A * | 1/1988 | Bordner | B65D 43/0258 |
| | | | 206/508 |
| 4,783,056 A | 11/1988 | Abrams | |
| 4,911,337 A | 3/1990 | Rosenthal | |
| 4,936,494 A | 6/1990 | Weidman | |
| 4,941,592 A | 7/1990 | Kitterman | |
| 4,942,966 A | 7/1990 | Kemp | |
| 5,038,957 A | 8/1991 | Gross | |
| D331,878 S | 12/1992 | Forsyth | |
| D334,538 S | 4/1993 | Bolen, Jr. et al. | |
| RE34,263 E | 5/1993 | vanKerkhoven et al. | |
| D339,065 S | 9/1993 | Forsyth et al. | |
| D340,187 S | 10/1993 | Forsyth | |
| 5,294,015 A | 3/1994 | Landis | |
| 5,295,599 A | 3/1994 | Smith | |
| 5,312,011 A | 5/1994 | Fischer | |
| 5,330,082 A | 7/1994 | Forsyth | |
| 5,499,736 A | 3/1996 | Kohl | |
| 5,667,094 A | 9/1997 | Rapchak et al. | |
| 5,769,253 A | 6/1998 | Gross | |
| 5,788,064 A | 8/1998 | Sacherer et al. | |
| 5,810,197 A | 9/1998 | Mazzarolo | |
| 5,911,937 A | 6/1999 | Hekal | |
| 6,039,197 A | 3/2000 | Braun | |
| 6,050,441 A * | 4/2000 | Kuo | B65D 43/168 |
| | | | 220/849 |
| 6,080,350 A | 6/2000 | Hekal | |
| 6,124,006 A | 9/2000 | Hekal | |
| 6,130,263 A | 10/2000 | Hekal | |
| 6,170,696 B1 | 1/2001 | Tucker et al. | |
| 6,192,895 B1 * | 2/2001 | Yuhara | A45D 40/22 |
| | | | 132/300 |
| 6,194,079 B1 | 2/2001 | Hekal | |
| 6,214,255 B1 | 4/2001 | Hekal | |
| D448,296 S | 9/2001 | Bried et al. | |
| 6,299,033 B1 | 10/2001 | Verweyst et al. | |
| RE37,634 E | 4/2002 | Hickman et al. | |
| 6,371,319 B2 | 4/2002 | Yeaton et al. | |
| 6,401,957 B1 * | 6/2002 | Przytulla | B65D 45/32 |
| | | | 220/654 |
| 6,486,231 B1 | 11/2002 | Hekal | |
| 6,510,971 B1 | 1/2003 | Martin | |
| D476,892 S | 7/2003 | Martin et al. | |
| 6,705,463 B1 | 3/2004 | Bucholtz et al. | |
| 6,752,092 B2 | 6/2004 | Beallie et al. | |
| D509,426 S | 9/2005 | Samz et al. | |
| 7,005,459 B2 | 2/2006 | Hekal | |
| D529,800 S | 10/2006 | Liebe | |
| 7,597,853 B2 | 10/2009 | West et al. | |
| 7,819,267 B2 | 10/2010 | Kick | |
| 8,083,094 B2 | 12/2011 | Caulfield et al. | |
| 8,297,457 B2 | 10/2012 | Kick | |
| 8,470,230 B2 | 6/2013 | Caulfield et al. | |
| 8,881,942 B2 * | 11/2014 | Giraud | B65D 83/0811 |
| | | | 220/849 |
| 8,899,443 B2 * | 12/2014 | Soibel | B65D 43/0233 |
| | | | 220/795 |
| 9,475,619 B2 | 10/2016 | Procter | |
| 9,532,636 B2 * | 1/2017 | Jung | A45D 40/221 |
| 9,718,587 B2 | 8/2017 | Harada et al. | |
| 9,834,341 B2 * | 12/2017 | Giraud | A61J 1/03 |
| 9,956,560 B2 | 5/2018 | Landes | |
| 11,498,737 B1 * | 11/2022 | Weir | B65D 77/046 |
| 2002/0104849 A1 | 8/2002 | Giraud | |
| 2002/0125203 A1 | 9/2002 | Bried et al. | |
| 2002/0148846 A1 * | 10/2002 | Luburic | B65D 43/162 |
| | | | 220/780 |
| 2002/0175173 A1 | 11/2002 | Diesterbeck | |
| 2003/0087015 A1 | 5/2003 | Wyslotsky et al. | |
| 2004/0124200 A1 * | 7/2004 | Yuhara | A45D 33/006 |
| | | | 220/849 |
| 2004/0173612 A1 | 9/2004 | Giraud | |
| 2004/0245261 A1 | 12/2004 | Stanos et al. | |
| 2005/0023183 A1 | 2/2005 | Banik et al. | |
| 2005/0067313 A1 | 3/2005 | Banik et al. | |
| 2005/0258180 A1 | 11/2005 | Lown | |
| 2007/0193891 A1 | 8/2007 | Portier | |
| 2007/0205196 A1 | 9/2007 | Burney et al. | |
| 2007/0262044 A1 | 11/2007 | Richir | |
| 2008/0035658 A1 | 2/2008 | Caulfield et al. | |
| 2008/0197134 A1 | 8/2008 | Maxwell | |
| 2009/0084805 A1 | 4/2009 | Bryson et al. | |
| 2011/0000930 A1 | 1/2011 | Logel et al. | |
| 2011/0127269 A1 | 6/2011 | Bucholtz et al. | |
| 2012/0024856 A1 | 2/2012 | Smyers | |
| 2012/0211493 A1 * | 8/2012 | Daggett | B65D 43/22 |
| | | | 206/508 |
| 2013/0068765 A1 | 3/2013 | Procter | |
| 2013/0161345 A1 * | 6/2013 | Tatin | A45D 40/0068 |
| | | | 220/348 |
| 2013/0256329 A1 | 10/2013 | Belfance et al. | |
| 2014/0319149 A1 | 10/2014 | Freedman et al. | |
| 2014/0319162 A1 * | 10/2014 | Bois | B65D 43/169 |
| | | | 220/849 |
| 2015/0008223 A1 | 1/2015 | Harada et al. | |
| 2015/0368003 A1 | 12/2015 | Freedman et al. | |
| 2015/0375918 A1 | 12/2015 | Holderness et al. | |

(56) References Cited

U.S. PATENT DOCUMENTS

| | | |
|---|---|---|
| 2016/0039955 A1 | 2/2016 | Klein et al. |
| 2016/0130045 A1 | 5/2016 | Giraud et al. |
| 2016/0318677 A1 | 11/2016 | Schneider |
| 2017/0108486 A1* | 4/2017 | Joseph .................. B65D 53/02 |
| 2017/0139216 A1* | 5/2017 | Crenko .................. B65D 41/06 |
| 2018/0362224 A1 | 12/2018 | Philip |
| 2019/0344943 A1* | 11/2019 | Gröner .................. B65D 51/20 |

FOREIGN PATENT DOCUMENTS

| | | |
|---|---|---|
| CN | 203064396 U | 7/2013 |
| CN | 103648922 A | 3/2014 |
| CN | 104053610 A | 9/2014 |
| CN | 104995101 A | 10/2015 |
| DE | 20006093 U1 | 9/2000 |
| EP | 09525088 A1 | 10/1999 |
| EP | 1805088 A1 | 4/2006 |
| EP | 2548466 A1 | 1/2013 |
| EP | 2796386 A | 10/2014 |
| GB | 2151591 A | 7/1985 |
| JP | 5298272 A | 10/1994 |
| JP | H11075933 A | 3/1999 |
| JP | 2004136933 A | 5/2004 |
| JP | 2007304098 A | 11/2007 |
| WO | 2004000680 A1 | 12/2003 |
| WO | 2005074571 A2 | 8/2005 |
| WO | 2006045087 A2 | 4/2006 |
| WO | 2014116622 A1 | 7/2014 |
| WO | 2014204890 A1 | 12/2014 |
| WO | 2016022744 A1 | 2/2016 |
| WO | 2016060755 A1 | 4/2016 |
| WO | 2016173891 A1 | 11/2016 |

\* cited by examiner

CONTAINER AND LID WITH MULTIPLE SEALS THEREBETWEEN AND METHODS FOR MAKING AND USING THE SAME

CROSS-REFERENCE TO RELATED APPLICATIONS

This application is a continuation application of U.S. patent application Ser. No. 16/834,176 filed Mar. 30, 2020, which is a continuation application of U.S. patent application Ser. No. 16/081,597 filed Aug. 31, 2018, which granted as U.S. Pat. No. 10,669,079, which is a U.S. National Phase of International Application No. PCT/US2017/021010 filed Mar. 6, 2017, which claims priority to U.S. Provisional Patent Application No. 62/419,275 filed Nov. 8, 2016 and U.S. Provisional Patent Application No. 62/303,483 filed Mar. 4, 2016, all of which are herein incorporated by reference in their entirety.

BACKGROUND OF THE INVENTION

1. Field of Invention

This invention relates generally to containers for products susceptible to degradation from moisture. More particularly, this invention relates to flip-top moisture tight containers which are simple to open and close repeatedly and which include two or more seals in series between the lid and the body which reliably provide moisture tightness after several cycles of opening and closing. Containers according to the present invention may be utilized for, e.g., pharmaceuticals, probiotics, nutraceuticals, diagnostic test strips and other moisture sensitive items.

2. Description of Related Art

The efficacy of medication may be compromised by moisture. As the medication absorbs moisture, the medication may become less effective for its intended purpose. Diagnostic test strips, such as blood glucose test strips that are used in diabetic care, can also be adversely affected by exposure to moisture.

Medication and/or test strips are typically stored in a container. Such a container may include a body that defines an interior for housing a product, and an opening leading to the interior. A cap or lid may also be included, optionally connected to the body by a hinge. By closing the lid on the body to cover and seal the opening, the container is closed and contents may be safely stored therein.

Products such as diagnostic test strips rely on certain environmental conditions to provide an accurate reading when used. If subjected to a certain moisture or relative humidity, these products can provide false readings with hi or low bias. Thus, moisture can significantly reduce the shelf life of these products. Consumers that require diagnostic test strip testing, such as the diabetic market, often test multiple times within a 24 hour period and depend on the accuracy of the readings they get.

Medication and diagnostic test strips can encounter moisture at multiple times in their life cycles. Such an encounter may occur during the manufacturing stage, during shipping, while the product is in storage prior to being sold, while the product is in storage after being sold, and each and every time a container containing the product is opened so that the product can be used. Even after products are stored in moisture tight containers, there still exists a small amount of moisture ingress through the seal, which over time can be deleterious to moisture sensitive contents inside. For this reason, a desiccant material (e.g., in the form of a desiccant entrained polymer) is typically provided in the container to absorb moisture. However, the desiccant material adds to the cost of manufacturing. An improved seal would translate to a reduced volume of desiccant to achieve the calculated moisture budget and thus a less expensive-to-manufacture container.

On the other hand, the seal itself should not significantly add to the cost of making the container or else the cost savings through reduced use of desiccant can be cancelled out. In addition, the seal itself must be carefully designed so that it does not require significant force to open while at the same time not being too easy to open such that the container could inadvertently pop open, e.g., due to pressure changes that may occur during transport. In the pharmaceutical and diagnostics packaging business, it is important to balance product improvements with manufacturing efficiencies and cost realities.

There is thus a need for an improved flip-top container for pharmaceutical or diagnostic test strip use, which is inexpensive to make and provides a reliably moisture-tight sealing effect after several cycles of opening and closing, without requiring high opening force to open.

SUMMARY OF THE INVENTION

Accordingly, a moisture tight container in accordance with an exemplary embodiment of the present invention is provided. The container has a container body having a base and a sidewall extending from the base. The body defines an interior configured for housing product, such as diagnostic test strips, for example. The body further has an opening leading to the interior. A lid is connected to the body by a hinge and is pivotable about the hinge with respect to the container body to move the container between a closed position in which the lid covers the opening so as to create a moisture tight seal with the body and an open position in which the opening is exposed. The moisture tight seal is provided by a plurality of engaged mating seals in series between the body and the lid when the lid is in the closed position. The plurality of engaged mating seals includes at least a first seal and a second seal. The first seal is formed by mating a thermoplastic sealing surface of the body to a thermoplastic sealing surface of the lid. The second seal is formed by mating a thermoplastic sealing surface of the body with an elastomeric sealing surface of the lid. The elastomeric sealing surface includes an elastomeric ring that is configured to be compressed by an upper surface of a rim surrounding the opening when the lid is in the closed position. Vertical compression of the elastomeric ring causes a portion of the ring to elastically expand radially into a void provided between the body and the lid.

A moisture tight container in accordance with another exemplary embodiment of the present invention thus includes a body and a lid. The body defines an interior for housing a product, and an opening leading to the interior. The lid is connected to the body with a hinge. The lid is movable with respect to the body between a closed position in which the lid covers the opening and is mated to the body, and an opened position in which the opening is exposed. A plurality of seals are located between the body and the lid. The seals are in series when the lid is in the closed position. The plurality of seals includes a first seal that requires an opening force to transition from the closed position to the opened position, and a second seal in combination with the first seal not requiring more than the opening force to transition from the closed position to the opened position. The first seal is formed by mating thermoplastic-to-thermoplastic sealing surfaces, and the first seal includes an undercut of the body relative to a central axis of the body. The second seal is formed by mating elastomer-to-thermoplastic sealing surfaces, and the elastomer-to-thermoplastic sealing surfaces includes an elastomer formed in the lid or on the body, optionally with multi-shot injection molding. The thermoplastic is incompressible and the elastomer is compressible and preferably resilient.

BRIEF DESCRIPTION OF SEVERAL VIEWS OF THE DRAWINGS

The invention will be described in conjunction with the following drawings in which like reference numerals designate like elements and wherein.

DETAILED DESCRIPTION OF PREFERRED EMBODIMENTS OF THE INVENTION

Figure 1:
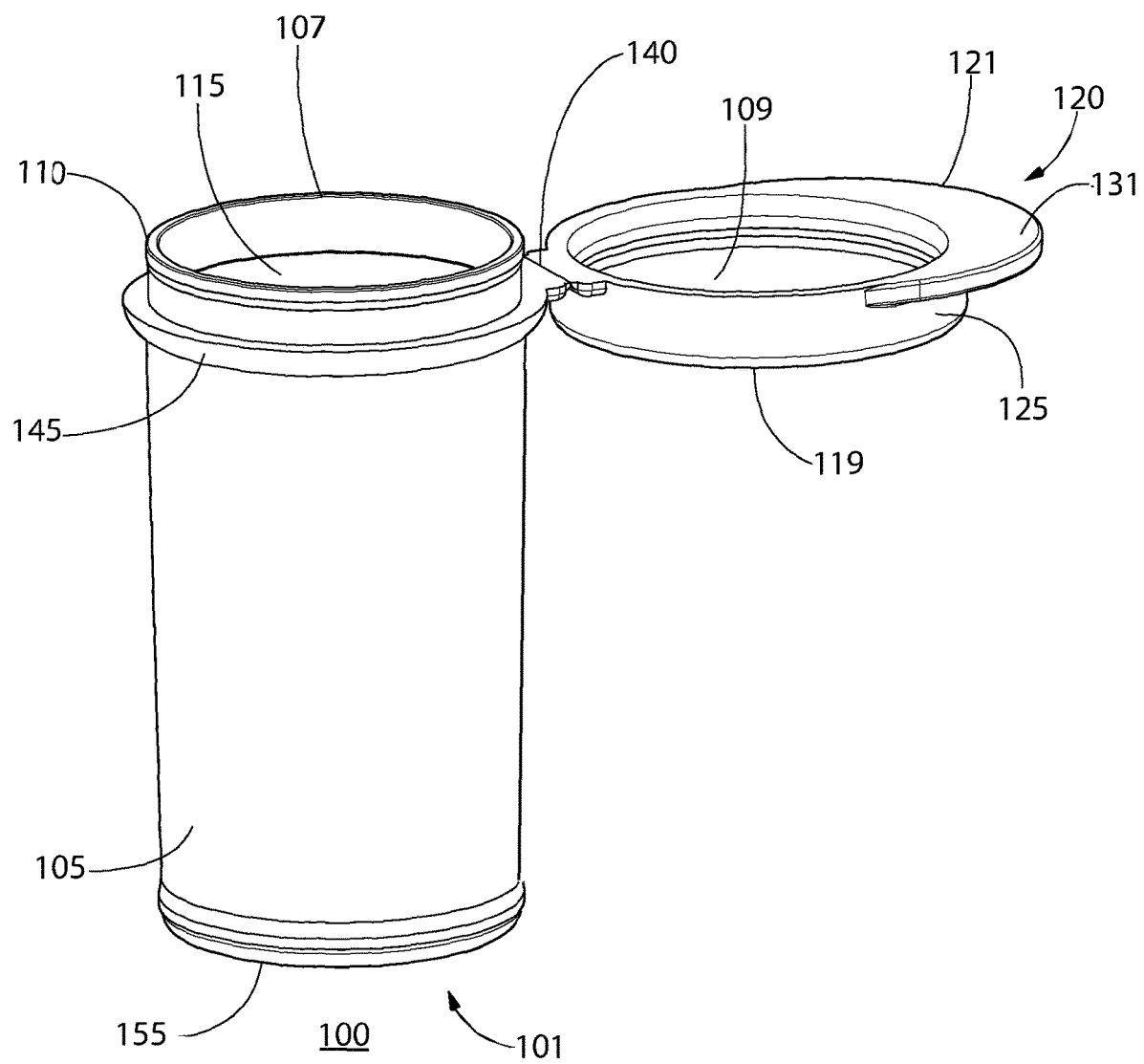
FIG. 1 is a perspective view of a container in accordance with an exemplary embodiment in an opened position.

Generally, the invention is directed to containers and methods for making the same for reducing the amount of moisture that enters a container between the container body and the lid that seals the body. In one aspect, the disclosed embodiments are configured to reduce the amount of moisture that can flow between the body and the lid by providing at least two seals in series, wherein one such seal is formed by an elastomer-to-thermoplastic interface, which uniquely does not increase force needed to open the container. As used herein, the term "elastomer" is to be understood in its broad sense. A particularly preferred elastomer is a thermoplastic elastomer (TPE), optionally one having a Shore A hardness of from 20 to 50, preferably from 20 to 40, more preferably from 20 to 35. Alternatively, the term "elastomer" may include silicone rubbers or other preferably injection moldable soft and resilient materials appropriate for creating a compression seal against a harder (e.g., thermoplastic) surface. In any embodiment, the elastomer should be configured for repeated use, i.e., should not degrade over several cycles (e.g., at least 10, preferably at least 25, more preferably at least 50 cycles) of opening and closing.

Optionally, the invention relates to a container produced in a multi-shot injection molding process wherein the elastomeric seal is produced in one shot and the thermoplastic container is produced in another shot. Container embodiments as disclosed herein preferably incorporate a hinged flip-top lid, wherein the body and lid include therebetween a low mass elastomer-to thermoplastic seal working in series with a thermoplastic-to-thermoplastic seal between the body and lid. The combined seals further reduce moisture vapor transmission into the container when closed than either seal alone, allowing for longer shelf life protection while still enabling the container to have a low opening force to benefit consumer use.

The external container is constructed of two materials, namely (primarily) a base thermoplastic (e.g., polypropylene) and an elastomer, preferably a thermoplastic elastomer (TPE) as one sealing surface of the invention. The container has an integrated lid connected to the body by a hinge, optionally a living hinge, which is designed to be easily opened and closed by the consumer. By nature of the material selection and thermoplastic-to-thermoplastic seal design, the container has a low moisture vapor transmission rate (MVTR). This container also incorporates an elastomer material to create an additional elastomer-to-thermoplastic seal to further reduce the MVTR. By further reducing the MVTR, the container requires less moisture protection via any method of desiccation to achieve a targeted shelf life. The combination of seals allows the container to provide a lower MVTR than an otherwise comparable reference container having only thermoplastic-to-thermoplastic sealing, and at the same time allows for a lower opening and closing force than would be expected when using a thermoplastic-to-elastomer seal alone. In addition, the low mass of elastomer material will still allow the recycle/re-use of the external container material in a container production process.

A thermoplastic hinge flip-top container in accordance with an exemplary embodiment of the present invention is constructed of materials with a low vapor transmission rate, e.g., polypropylene. In addition, the container lid is designed with a sealing mechanism that incorporates both a thermoplastic-to-thermoplastic seal in combination with a thermoplastic-to-elastomer seal that is permanently produced optionally inside the lid seal area, optionally via multi shot injection molding. The thermoplastic-to-thermoplastic seal area may be designed with an undercut at an angle (or rounding or slope) to the center axis of the vial that is not only part of the thermoplastic-to-thermoplastic seal, but due to the geometry, also controls the opening and closing force of the vial. By having the thermoplastic-to-thermoplastic seal work in series with the thermoplastic-to-elastomer seal, the compression force necessary to be applied to the thermoplastic seal to achieve the same level of moisture ingress may, in an optional aspect of the invention, be reduced. This may facilitate reduction of opening and closing force, thus making the container easier to use for the consumer. This is particularly useful for consumer populations that may have difficulty in opening and closing containers such as patients with diabetic neuropathy, or senior citizens.

A thermoplastic-to-thermoplastic seal relies on the mating of two incompressible surfaces that must match geometrically very closely in order to provide a closing relationship (e.g., snap-fit) and to act as an effective moisture barrier. This requires sufficient compression force to mate the opposing incompressible surfaces, thus forming the seal. The effectiveness of the seal is dependent on the area of contact and the amount of air space (e.g., through microgaps or due to imperfections or wear and tear of the thermoplastic material) between the surfaces that allow moisture to pass through.

A thermoplastic-to-elastomer seal relies on one incompressible surface (the thermoplastic surface) mating with a compressible and preferably resilient surface (the elastomeric surface). This type of seal relies on generating sufficient force between the surfaces to compress the elastomer such that it "fills" any possible gaps or imperfections in the opposing incompressible surface. This pressure must be maintained at all times when the container is closed to provide moisture tightness and then overcome in order to open the container.

By combining a thermoplastic-to-thermoplastic seal in series with a thermoplastic-to-elastomer seal, the moisture vapor ingress can be reduced while still maintaining the container opening force in a range that is ergonomically advantageous to the consumer population.

In one optimal aspect of the embodiments disclosed herein, the elastomer-to-thermoplastic seal is configured and oriented such that the direction of compression of the seal is parallel with the main axis of the vial and vertical to the seal surface. This is the case whether the elastomer is on an inner portion of the vial lid, on an outer rim projecting radially from the vial body or on a top edge of the vial body disposed around the opening (or optionally two or all three of the foregoing). This way when the vial is opened and closed, the elastomer-to-thermoplastic seal is not subject to radial forces that can rub the elastomer and scarf or damage the seal (which may occur if such seal was on the side of the vial rim or on the inner skirt of the vial lid). This enables repeated openings without deteriorating performance of the elastomer-to-thermoplastic seal. This configuration enables the use of a lower durometer seal material which requires less compression force and again provides lower opening force with lower ingress rates than a reference vial that is otherwise identical but for the elastomer-to-thermoplastic seal. In addition, this configuration does not increase the opening force of the seal, unlike a stopper-type seal with a radially compressed elastomeric element.

Referring now in detail to the various figures of the drawings wherein like reference numerals refer to like parts, there is shown in FIG. 1 a container that may be used in combination with various features in order to provide exemplary embodiments of the present invention. Container 100 may be made primarily from one or more injection moldable thermo-plastic materials, including, for example, a polyolefin such as polypropylene or polyethylene. According to an optional embodiment, the container may be made from a mixture comprising primarily thermo-plastic material and a very small proportion of thermoplastic elastomer material.

Container 100 includes a container body 101 having a base 155 and an optionally tubular sidewall 105 extending therefrom, the body 101 defining an interior 115 configured for housing product, e.g., diagnostic test strips. The sidewall 105 optionally terminates at a lip 110 having a top edge, the lip 110 surrounding an opening 107 of the body 101, leading to the interior 115.

A lid 120 is preferably connected to the body 101 by a hinge 140, optionally a living hinge, creating a flip-top container 100 or vial. The lid 120 is pivotable about the hinge 140 with respect to the container body 101 to move the container between a closed position (see, e.g., FIG. 4 or 5) in which the lid 120 covers the opening 107 (preferably so as to create a moisture tight seal with the body) and an open position (see, e.g., FIG. 1) in which the opening 107 is exposed.

Container body 101 may optionally include outer rim 145 that projects radially outward from the sidewall 105 and completely encircles container body 101 near a top thereof. Optionally, the lip 110 projects vertically from the rim 145. Optionally, in any embodiment, the lip 110 has a thickness approximately equal to the remainder of the sidewall 105. Optionally, in any embodiment, the lip 110 has a thickness slightly less than that of the remainder of the sidewall 105.

Lid 101 includes a lid base 119 and preferably a depending skirt 125. Lid 101 further includes a lid outer rim 131 and optionally a thumb tab 121 extending radially from the lid 120. In order to close container 100, the lid 120 is pivoted about the hinge 140 so that the lid 120 covers the opening 107 and engages respective mating sealing surfaces of the lid 120 and body 101, to place lid 120 in closed position.

Figure 2:
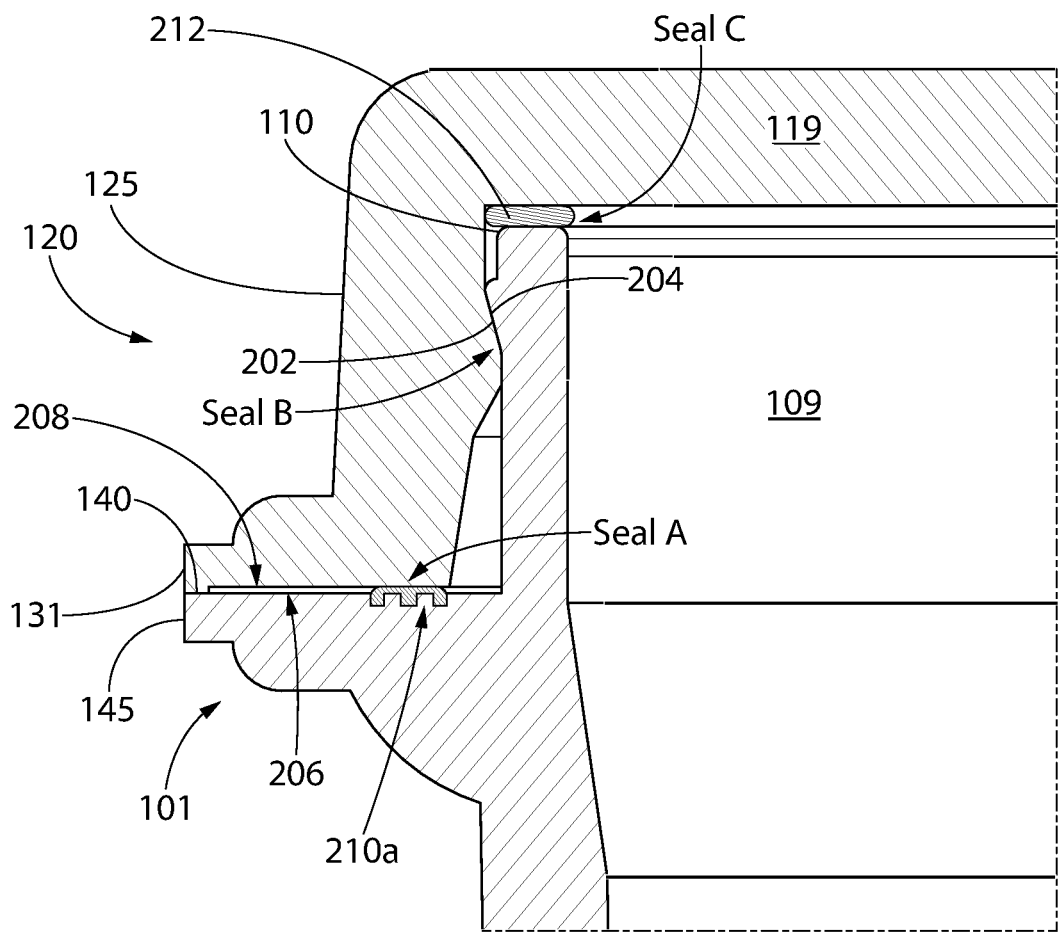
FIG. 2 is an enlarged cross-sectional view which illustrates a first variation of the exemplary embodiment of FIG. 1.

FIG. 2 is a sectional view of a container in accordance with a first variation of the exemplary embodiment of FIG. 1. Body 101 is shown near the bottom of the figure while lid 120 is shown near the top of the figure. As discussed above with respect to FIG. 1, the body 101 optionally includes outer rim 145 which projects radially about the circumference of body 101 and near the top of body 101. Lid 120 includes lid outer rim 131, optionally projecting radially from the inner portion of the depending skirt 125 of the lid 120.

When the lid 120 is in the closed position, lid rim surface 208 faces body rim surface 206. Thus, when lid 120 is in the closed position, body rim surface 206 and at least portions of lid rim surface 208 engage each other. Affixed to body rim surface 206 is elastomer seal 210a. The seal 210a is preferably an annular ring disposed around the circumference of body rim surface 206. In the illustrated exemplary embodiment, an elastomer-to-thermoplastic seal is created by elastomer seal 210a engaging and being compressed by lid rim surface 208.

Lid 120 includes lid interior 109, defined by lid base 119 and skirt 125. The lip 110 of body 101 extends into lid interior 109 when the lid 120 is in the closed position. In that position, body undercut surface 204 of body 101 mates with lid undercut surface 202. Accordingly, a thermoplastic-to-thermoplastic sealing surface is formed. In addition, this configuration provides a closing position, e.g., via a snap-fit mating configuration, to retain the lid 120 in the closed position and prevent it from inadvertently opening. As shown in FIG. 2, the thermoplastic-to-thermoplastic seal and the closing position are formed by respective undercut surfaces 204, 202. This may be defined, for example, with reference to an axis 400 (see FIG. 4) extending through a center of body 101 along its length. Lid undercut surface 202 and body undercut surface 204 are not parallel to that axis 400. Rather, as shown, lid undercut surface to 202 and body undercut surface 204 are formed at a slight angle, e.g., from 10° to 30° relative to the axis 400. Optionally, the respective undercut surfaces may alternatively be complimentarily rounded or sloped to mate with each other. With any such undercut configuration, if a user attempts to lift the lid 120 from body 101 to transition the lid 120 to an opened position, an opening force will be required to overcome the force between lid undercut surface 202 and body undercut surface 204 when the lid 120 is in the closed position.

In the exemplary embodiment shown in FIG. 2, lid 120 is shown as optionally including lid elastomer seal 212, which is optionally in the form of an annular ring affixed to lid base 119 adjacent to or abutting skirt 125. Thus, a seal may be formed between lid elastomer seal 212 and top edge 110. This creates an elastomer-to-thermoplastic seal between lid elastomer seal 212 and top edge 110 when the lid 120 is in the closed position. Optionally, the invention may omit either elastomer seal 212 or elastomer seal 210, thus providing only a single elastomer-to-thermoplastic seal in an optional embodiment.

It is contemplated that embodiments according to aspects of the invention may include multiple and different seals in series between lid 120 and body 101. For example, the seals may comprise the seal between lid undercut surface 202 and body undercut surface 204 and the seal between elastomer seal 210a and lid rim surface 208. Alternatively, the two seals may comprise the seal between lid undercut surface 202 and body undercut surface 204 and the seal between lid elastomer seal 212 and top edge 110. While three seals (labeled as Seal A-C) are shown in FIG. 2, this is merely exemplary, as two seals or greater than three seals may be included in accordance with exemplary embodiments of the invention. For example, it is possible for there to be a total of three seals, more than three cells, or only two seals as explained above. Furthermore, at least one of the seals is an elastomer-to-thermoplastic seal and at least one of the seals is a thermoplastic-to-thermoplastic seal. In other words, any two (or more) of the three seals shown may be included, as long as a combination of elastomer-to-thermoplastic and thermoplastic-to-thermoplastic is included.

It should further be noted that the thermoplastic-to-thermoplastic seal provides the compression force needed to maintain the elastomer-to-thermoplastic seal. This configuration does not require that the elastomer-to-thermoplastic seal be a source of radial compressive force (e.g., as is the case with an elastomeric stopper plugged into a tube). As such, the elastomer-to-thermoplastic seal does not add to the opening force necessary to overcome the thermoplastic-to-thermoplastic seal to transition the lid 120 from the closed position to the opened position. In fact, resilience of the compressed elastomer when the lid 120 is in the closed position may result in a slight vertical spring force biasing the respective undercut surfaces 202,204 vertically against each other, thus reinforcing or strengthening the thermoplastic-to-thermoplastic seal. Thus, if anything, such slight vertical spring force created by the elastomer-to-thermoplastic seal may tend to actually reduce the opening force compared to an otherwise identical container without an elastomeric sealing surface.

Figure 3:
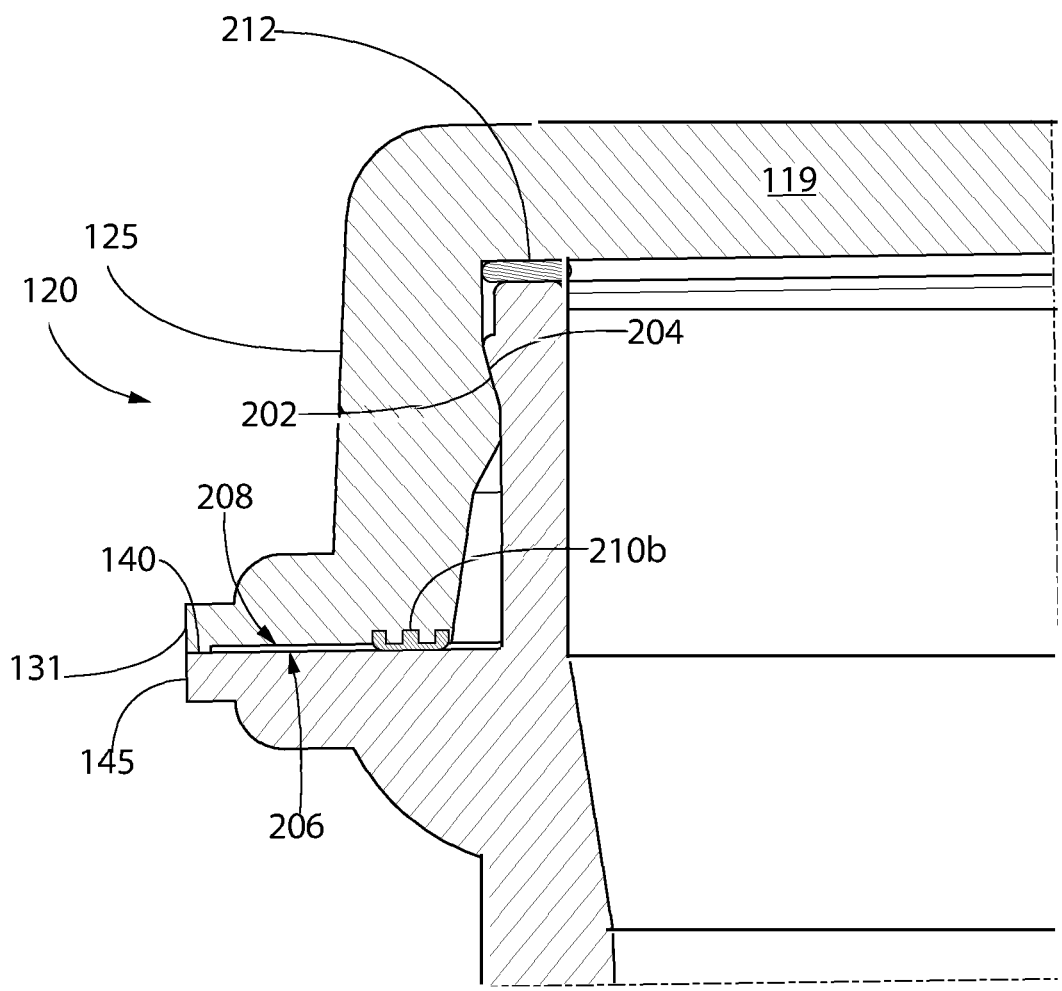
FIG. 3 is an enlarged cross-sectional view which illustrates a second exemplary embodiment of the exemplary embodiment of FIG. 1.

As discussed above with respect to the exemplary embodiment shown in FIG. 2, elastomer seal 210a is affixed to an upper surface of outer rim 145 of the body 101. FIG. 3 shows an alternative exemplary embodiment in which elastomer seal 210b is affixed to lid outer rim 131 and is in contact with outer rim 145 of body 101. In this manner, with regard to the embodiment of FIG. 2 and the embodiment of FIG. 3, an elastomer-to-thermoplastic seal is formed.

Figure 4:
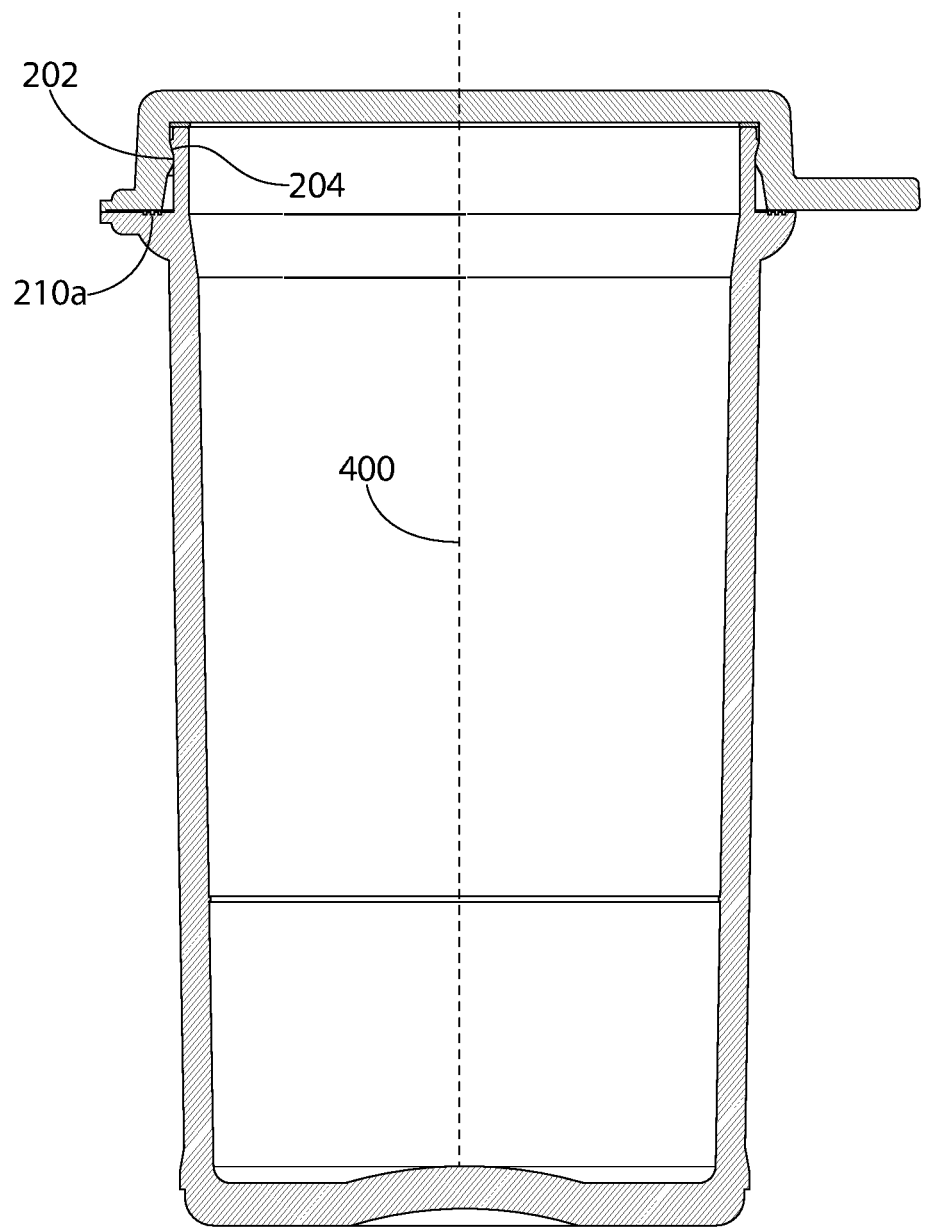
FIG. 4 is a cross-sectional view which illustrates the features of FIG. 2 and further shows additional portions of a container in accordance with the first variation of the exemplary embodiment of FIG. 1.

FIG. 4 shows the seals which are illustrated in FIG. 2 and further illustrates more of body 101 that is shown in FIG. 2. FIG. 4 is helpful for illustrating the relationship between the sealing surface that is formed between lid undercut surface 202 and body undercut service 204 and central axis 400 which runs along the length of body 101 and through its center. As can be seen in FIG. 4, lid undercut surface 202 and body undercut surface 204 form an undercut because the seal between these two surfaces is not parallel to central axis 400. In this manner, the undercut between lid undercut surface 202 and body undercut service 204 includes compression force vectors in both vertical and horizontal directions. The vertical compression force vector requires that an opening force be applied in order to separate lid 120 from body 101 and thus transition the lid 120 from the closed position to the opened position.

Figure 5:
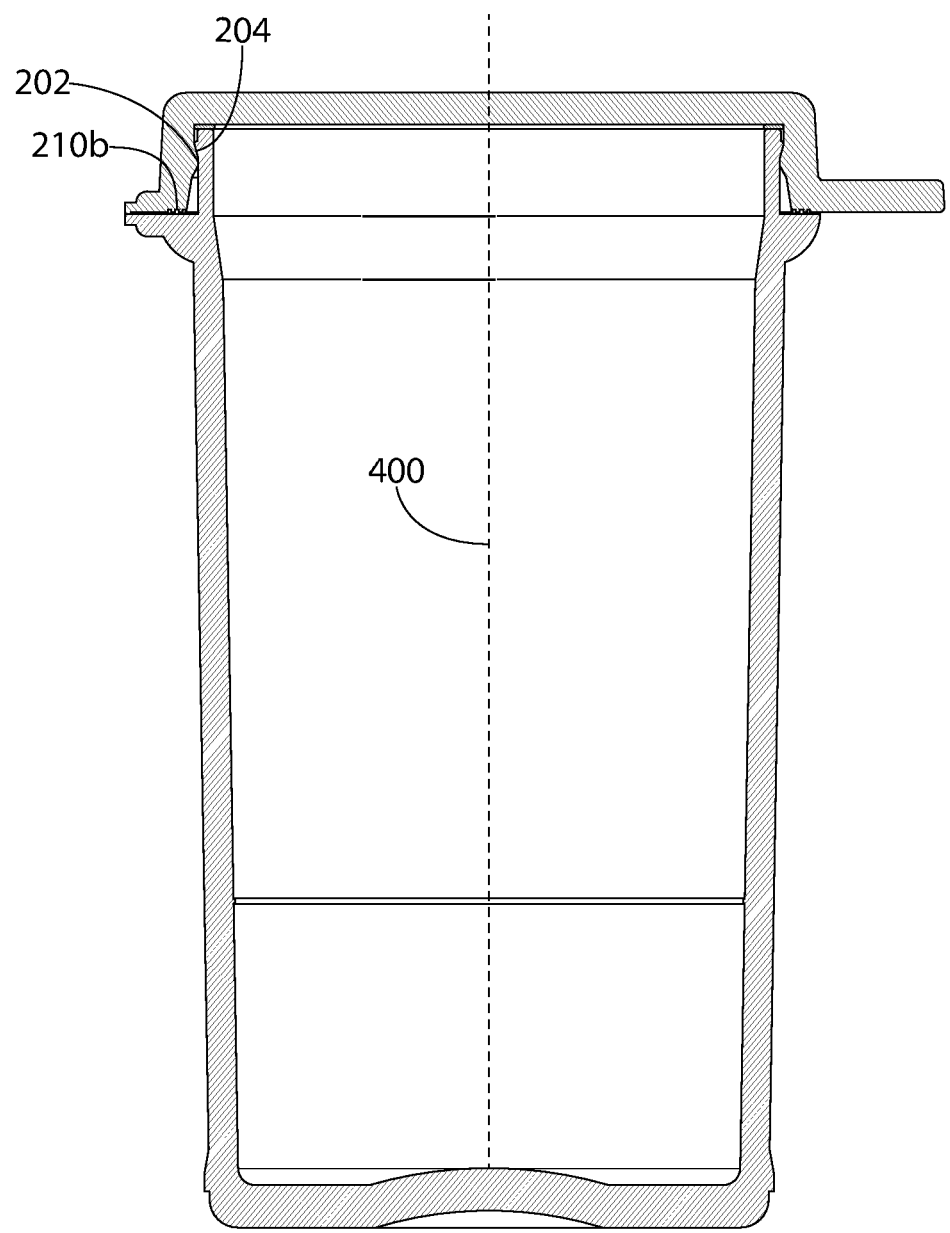
FIG. 5 is a cross sectional view which illustrates the features of FIG. 3 and further shows additional portions of a container in accordance with the second variation of the exemplary embodiment of FIG. 1.
Figure 6:
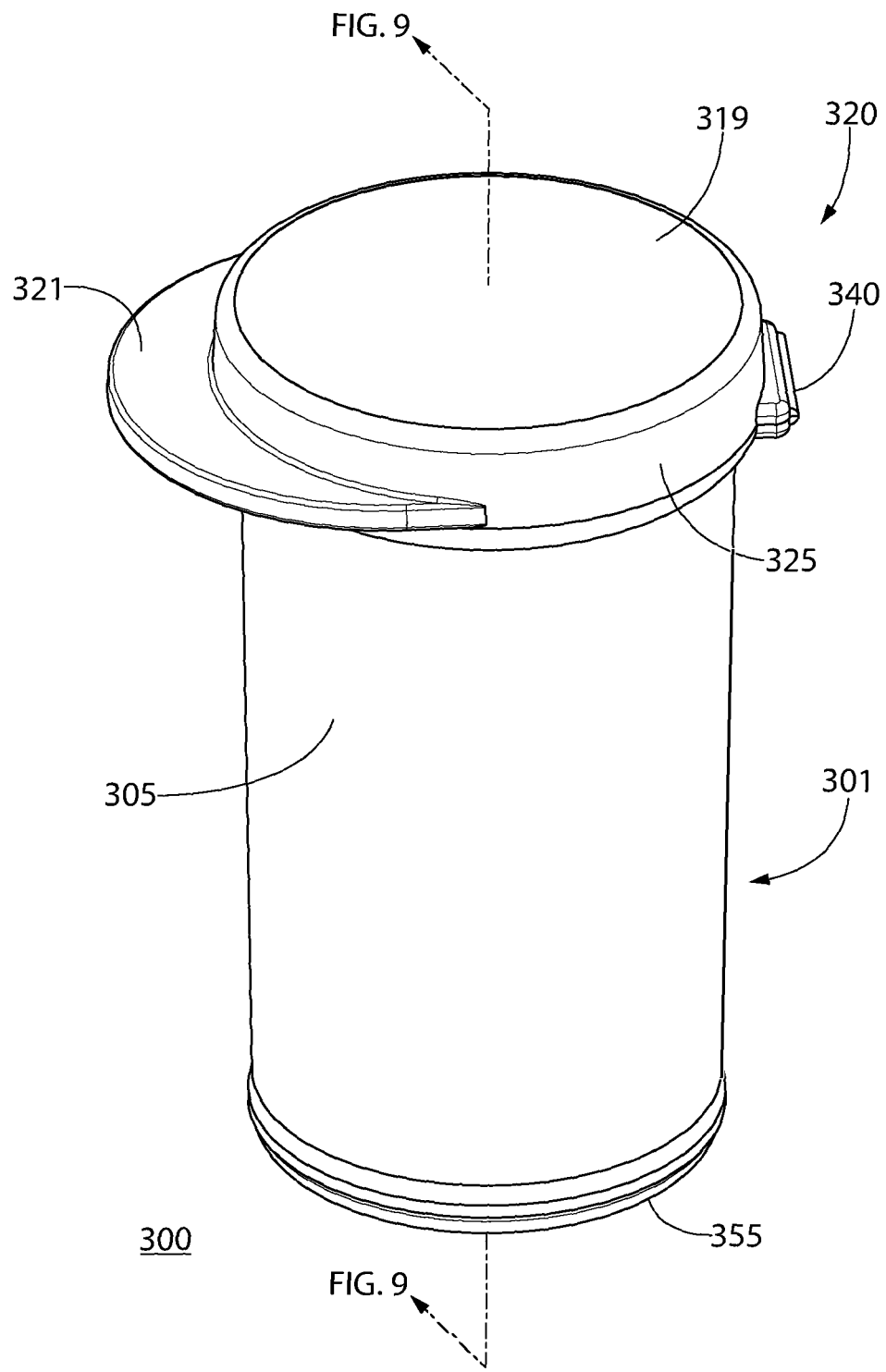
FIG. 6 is a perspective view of a container in accordance with a second exemplary embodiment in a closed position.
Figure 7:
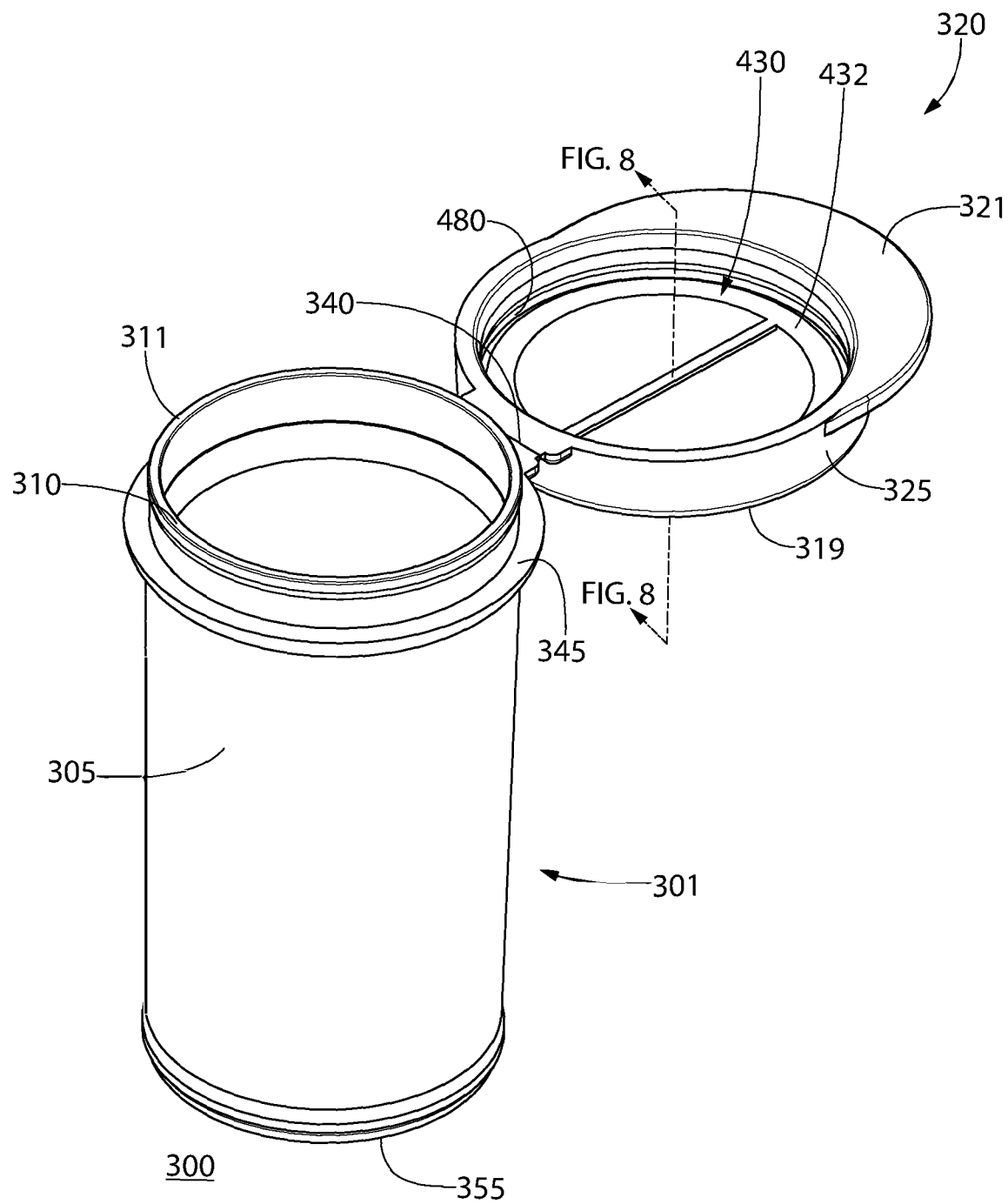
FIG. 7 is a perspective view of the container of FIG. 6 in an opened position.
Figure 8:
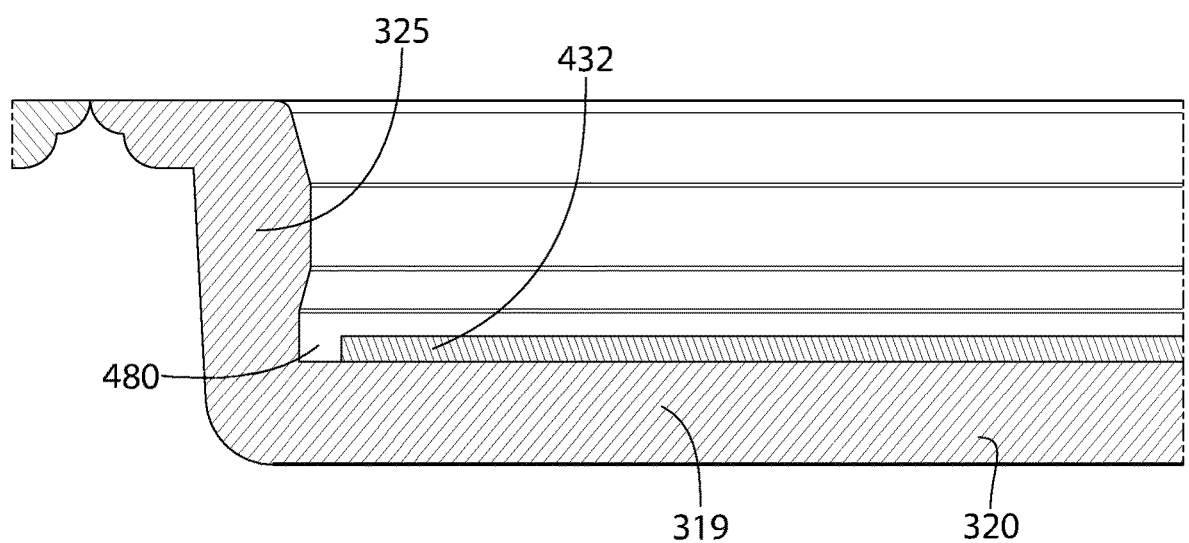
FIG. 8 is an enlarged cross sectional view taken along section line 8-8 of the container of FIG. 7 illustrating sealing surfaces in the lid.

FIG. 5 shows the seals which are illustrated in FIG. 3 and further illustrates more of body 101 that is shown in FIG. 3. FIG. 5 is also helpful for illustrating the relationship between the sealing surface that is formed between lid undercut surface 202 and body undercut surface 204 and central axis 400 which runs along the length of body 101 and through its center. The configuration and function of respective undercut surfaces 202,204 of lid 120 and body 101 are identical to those shown in FIG. 4 and are not rehashed here for the sake of brevity.

The combination of a thermoplastic-to-thermoplastic seal in series with an elastomer-to-thermoplastic seal according to an optional aspect of the invention provides an MVTR through the sealing system of a maximum of optionally 42 μg/day-cm of seal circumference/day when the ambient conditions are a minimum of 30° C./80% relative humidity (RH) externally and a maximum of 30° C./1% RH internally, while allowing for an opening force of optionally no greater than 3 N/cm of seal circumference.

Referring now to FIGS. 6-10B, there is shown a second exemplary embodiment of a container 300 according to an optional aspect of the invention. Many features of the container 300 of FIGS. 6-10B are similar or identical to corresponding features of the container 100 of FIGS. 1-5. Therefore, only a general summary is provided here of such similar or identical corresponding features as with the previously described embodiments. However, key differences as between the embodiments and additional embellishments are noted.

Container 300 includes a body 301 having a base 355 and optionally a sidewall 305 extending from the base. The body 301 defines an interior 315. The sidewall 305 optionally terminates at a lip 310 having a top edge 311. The lip 310 surrounds an opening 307 of the body 301, leading to the interior 315. In the embodiment shown, container body 301 includes outer rim 345. The lip 310 optionally projects vertically from the rim 345.

A lid 320 is preferably connected to the body 301 by a hinge 340, optionally a living hinge, creating a flip-top container 300 or vial. The lid 320 is pivotable about the hinge 340 with respect to the container body 301 to move the container 300 between a closed position and an open position. In the embodiment shown, lid 301 includes lid base 319 and preferably a depending skirt 325 and thumb tab 321.

When the lid 320 is in the closed position, a moisture tight seal 460 is formed by a plurality of engaged mating seals in series, including at least a first seal 462 and a second seal 464. The first seal 462 is formed by mating a thermoplastic sealing surface of the body 301 with a thermoplastic sealing surface of the lid 320. The first seal 462 is configured to require an opening force to disengage. In the optional embodiment shown, the first seal 462 comprises the engagement of undercut surface 404 of body 301 with undercut surface 402 of lid 320. This seal is identical to the undercut-to-undercut seal disclosed above with respect to the container 100 of FIGS. 1-5 and will thus not be elaborated upon further here.

Figure 9:
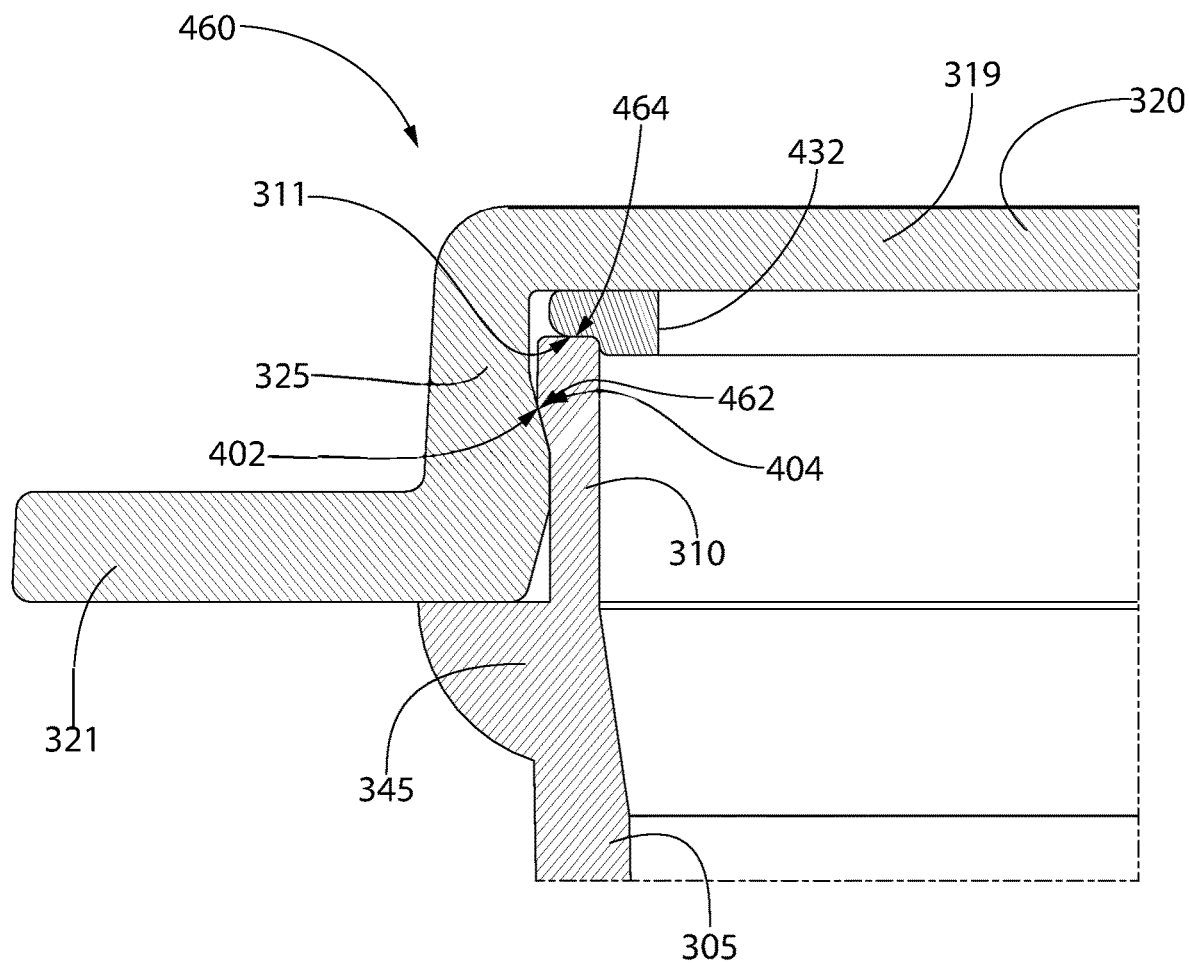
FIG. 9 is an enlarged cross sectional view taken along section line 9-9 of the container of FIG. 6 illustrating engagement of first and second seals in series to create a moisture tight seal.
Figure 10A:
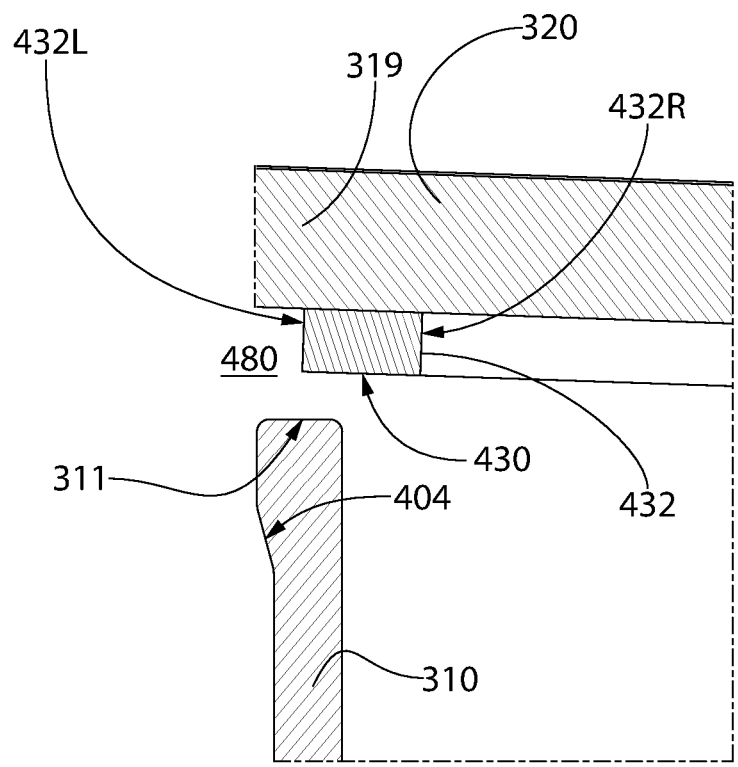
FIGS. 10A and 10B are schematic illustrations showing the elastomeric ring of the lid immediately before engagement with the thermoplastic sealing surface of the body (FIG. 10A) followed by sealing engagement of the elastomeric ring of the lid with the thermoplastic sealing surface of the body (FIG. 10B).
Figure 10B:
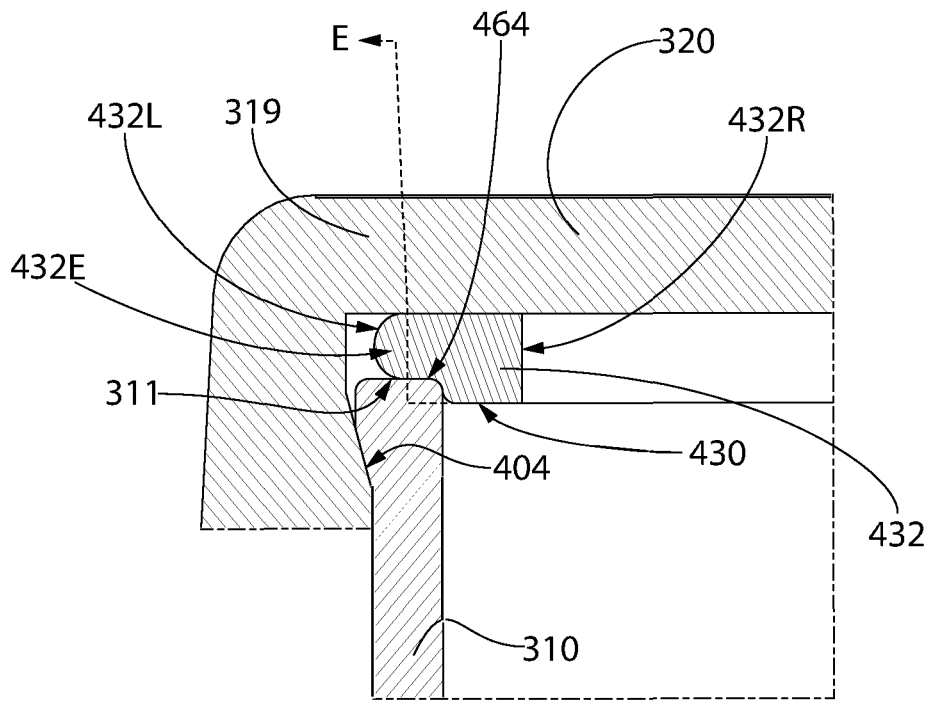

The second seal 464 is formed by mating a thermoplastic sealing surface of the body 301 or lid 320 with an elastomeric sealing surface of the body 301 or lid 320. In the optional embodiment shown, the second seal 464 is formed by mating a thermoplastic sealing surface of the body 301 with an elastomeric sealing surface of the lid 320. The elastomeric sealing surface 430 comprises an elastomeric ring 432 configured to be compressed by a thermoplastic upper surface 311 of a lip 310 surrounding the opening 307 when the lid 320 is in the closed position. As best shown in FIGS. 9-10B, vertical compression of the elastomeric ring 432 causes a portion of the ring 432 to elastically expand radially into a void 480 provided between the body 301 and the lid 320. This operation is now explained in detail.

The term "ring" as used herein can refer to an annular round element with a central opening. However, a "ring" is not necessarily limited to such configuration and could include non-round configurations as well as elastomeric elements that are filled in, at least in part, in the center (i.e., where an opening of a ring may otherwise be). As such, a "ring" could include a disc-shaped elastomeric member, for example.

FIG. 9 shows a partial enlarged cross section of the container 300 with the lid 320 in the closed position. As shown, the first seal 462 is provided, comprising the engagement of undercut surface 404 of body 301 with undercut surface 402 of lid 320. The second seal 464 comprises engagement of the thermoplastic upper surface 311 of the lip 310 with an engagement surface 430 of the elastomeric ring 432 provided on the underside of the base 319 of the lid 320. As can be seen in FIG. 9, a compression seal provided between the upper surface 311 of the lip 310 and the elastomeric ring 432 causes the cross section of the ring 432 to appear slightly stepped or indented along the engagement surface 430 of the elastomeric ring 432. This indent is more pronounced in the enlarged view shown in FIG. 10B. FIG. 10A shows the cross section of the ring 432 immediately before it contacts the upper surface 311 of the lip 310 to form the second seal. As shown in 10A, the ring 432, when not engaged with the lip, does not have such an indent. The indent in the engagement surface 430 of the elastomeric ring 432 is the product of elastomeric deformation of the ring 432 resulting from sealing engagement with the rim 310.

Notably, the elastomeric ring 432 is not bounded or blocked on either an immediate right side $432_R$ or left side $432_L$ thereof. As such, when the elastomeric ring 432 is compressed vertically, a portion thereof elastically expands or migrates radially outward, inward or both. A void 480 is provided, e.g., between the elastomeric ring 432 and the skirt 325 of the lid 320 to provide "living space" for the ring material to radially expand when the second seal 464 is engaged. FIG. 10B illustrates the radially expanded portion $432_E$ of the elastomeric ring 432 (shown expanded in direction E of FIG. 10B), occupying a portion of the void 480. To the extent such expansion appears in the Figures to be exaggerated compared to actual implementation, it is merely for illustrative purposes. This radial expansion into the void feature provides at least two important functions.

First, it results in tempering the vertical spring force between the elastomer and the rim. While it is desired that some slight spring force is provided to strengthen or reinforce the first seal, excessive spring force may tend to reduce the opening force to an extent that the container may inadvertently pop open. A balance must be struck between a desirably low opening force on the one hand (especially for elderly and/or diabetic users) and an opening force that is so low that it can result in inadvertent container openings, e.g., via common pressure variations that may occur within the container during transport. When the elastomer is permitted to expand radially, the vertical spring force may thus be provided at an acceptable level.

The second important function is that the surface area of contact between the sealing surfaces of the second seal increases via radial expansion of the ring's elastomeric material. This increase of the elastomer-to-thermoplastic sealing surface area provides a tighter seal at the site of engagement of the second seal.

It should be understood that any of the seal configurations disclosed in FIGS. 1-5 may be combined with those disclosed in FIGS. 6-10B.

Ingress Performance for the seal alone is measured by taking the total vial ingress rate and subtracting out the MVTR (moisture vapor transmission rate) through the thermoplastic comprising the outer shell of the vial.

In an exemplary embodiment, when the lid is in the closed position, the moisture vapor transmission rate MVTR is less than 370 µg/day at 30° C./80% RH (relative humidity). In an exemplary embodiment of a 24 ml vial according to embodiments of the invention, the weight of a desiccant entrained three phase polymer sleeve is 2.5-3.25 grams (optionally about 3.0 g) and the moisture ingress is about 400 micrograms per day at 30° C./70% RH. In an exemplary embodiment of a 17 ml vial according to embodiments of the invention, the weight of a desiccant entrained three phase polymer sleeve is 2.0-2.75 grams (optionally about 2.5 g) and the moisture ingress is about 300 micrograms per day at 30° C./70% RH. The term "three phase polymer" refers to a desiccant entrained polymer comprising a base polymer, desiccant and channeling agent, e.g., as described in U.S. Pat. Nos. 5,911,937, 6,080,350, 6,124,006, 6,130,263, 6,194,079, 6,214,255, 6,486,231, 7,005,459, and U.S. Pat. Pub. No. 2016/0039955, each of which is incorporated herein by reference as if fully set forth. Advantageously, in an optional aspect of the invention, the second seal permits reduced use of such desiccant material, resulting in lower manufacturing costs.

Broadly speaking, the term "moisture-tight" is defined as having a moisture ingress (after three days) of less than 1500 µg of water, in another embodiment, less than 500 µg of water, in a further embodiment, less than 300 µg of water, in yet another embodiment, less than 150 µg of water, as determined by the following test method: (a) place one gram plus or minus 0.25 grams of molecular sieve in the container and record the weight; (b) fully close the container; (c) place the closed container in an environmental chamber at conditions of 80% relative humidity and 72° F.; (d) after one day, weigh the container containing the molecular sieve; (e) after four days, weigh the container containing the molecular sieve; and (f) subtract the first day sample from the fourth day sample to calculate the moisture ingress of the container in units of micrograms of water.

In an exemplary embodiment, when the first seal and the second seal combined provide the container when the lid is in the closed position a lower MVTR than the first seal would provide without the second seal.

In an exemplary embodiment, when the first seal and the second seal combined provide the container when the lid is in the closed position a lower MVTR than the second seal would provide without the first seal.

In an exemplary embodiment of the present invention, the container is used for storing diagnostic test strips.

In an exemplary embodiment of the present invention, at least one of the thermoplastic-to-thermoplastic sealing surfaces is on a radially-projecting rim along an outside of the body.

In an exemplary embodiment of the present invention, the elastomer has a Shore A hardness from 20 to 50, preferably from 20 to 40, more preferably from 20 to 35. A skilled person in the art of injection molding would typically avoid using TPE materials with less than 50 shore A hardness for container seals. This is because such soft TPE materials are generally difficult to adhere to the base polymer without damaging or displacing the seal during molding. However, through molding techniques that Applicants developed, use of TPE materials with a hardness of less than 50 shore A for a container seal is made possible. Use of such low durometer material creates lower resistance to flow during molding, advantageously creates lower resistance to flow during molding, enabling a thinner cross section. It is less prone to creating knit lines in the finished seal that could adversely impact seal integrity. In addition, the softer TPE material requires less compression force to seal, which reduces the likelihood of excessive vertical spring force, which could otherwise result in inadvertent opening of the container as discussed above.

In the design of a flip top container the cap opening force is a critical to quality characteristic of the product. The acceptable range of opening force is 3 to 7 lbf (pound-force) when measured by affixing the body of the vial standing on the vial base and then applying an upward force to the underside of the bill of the cap, parallel to the axis of the vial at a constant speed of 500 mm/min at a controlled temperature of 20+/−2° C., with a preferred range of 4 to 6 lbf. As discussed above, a container that is too easy to open may open inadvertently and a container with an opening force above this range may be too difficult for the user to open.

The resistance to opening under differential pressure can optionally be measured by placing a container which has been opened and closed in the ambient environment into a sealed chamber and then reducing the external pressure in the chamber over a period of 30 seconds to one minute to create a differential pressure between the interior of the container and the external environment of at least 450 mBar, which is the maximum pressure differential a container should be exposed to during commercial air transportation.

In an exemplary embodiment of the present invention, the elastomer has a thickness of from 0.5 mm to 1.25 mm and optionally an exposed width of the outside vial rim is from 0 mm to 2.5 mm.

A vial in accordance with an exemplary embodiment of the present invention may be recycled after use. The recycling references the primary material and the chasing arrow corresponds to that recycle class. The vial lid seal with thermoplastic elastomer is designed with a lower mass of elastomer to still allow the container to be re-used/recycled along with the primary material designation.

An additional elastomer seal thus reduces the moisture vapor transmission rate through the vial container lid seal to allow less required desiccant mass. A combination of seals working in series enables reduced moisture vapor transmission, in combination with low lid opening and closing force to optimize the consumer experience. A low mass of elastomer within the vial lid seal to allow vial re-use/recyclability of the vial's primary material.

It is noted that while exemplary embodiments are shown as round containers with round seals, the invention is not limited thereto. It is contemplated that the present invention can also be utilized in the context of non-round flip-top containers to improve seal integrity between body and lid. In fact, it is contemplated that the elastomer-to-thermoplastic seals described herein would be particularly useful in enhancing seal integrity for non-round containers. For example, the first and second seals as disclosed herein may be utilized in elliptical containers, square containers, rectangular containers, quadrilateral containers with rounded corners and many other shapes. Optionally, embodiments of the present invention are utilized with container shapes and configurations disclosed in U.S. Pat. Pub. No. 2011/0127269, which is incorporated by reference herein in its entirety.

It is further noted that the thermoplastic-to-thermoplastic seal (e.g., the first seal 462) is not necessarily limited to the configuration as shown in the accompanying drawing figures. For example, in an optional aspect, the thermoplastic-to-thermoplastic seal may be provided between an inner polymer ring depending from the underside of the lid base and interfacing with a portion of the inner surface of the container body wall. Optionally, in such an embodiment, an annular protrusion of the inner polymer ring engages a radial undercut within the inner surface of the container body wall to create a variation of the first seal 462 disclosed with respect to FIGS. 6-10B. This variation of the first seal would likewise require overcoming an opening force to disengage that seal.

EXAMPLES

The invention will be illustrated in more detail with reference to the following Examples, but it should be understood that the present invention is not deemed to be limited thereto.

Example 1

Tests were run to measure moisture ingress of 24 ml vials according to the container embodiment shown in FIGS. 6-10B (Group A). Ambient conditions were set at 30° C. and 80% relative humidity. There were 48 such containers in the tested population. These moisture ingress results were compared against testing data gathered from testing a population of 7553 containers (Group B) that were identical in material respects to the containers of Group A, except the containers of Group B only included the first seal (plastic-to-plastic)— not the second seal (elastomer-to-plastic). The following table shows a side-by-side comparison of the data collected.

| Group | Mean Ingress (µg/day) | Standard Deviation (µg/day) | Sample Size |
|---|---|---|---|
| A | 399.8 | 22.61 | 48 |
| B | 440.9 | 105.5 | 7553 |

As the data show, the addition of the second seal resulted in a meaningful reduction of the mean ingress and a surprisingly significant reduction in the standard deviation of moisture ingress. This significant reduction in standard deviation is notable and important from a production standpoint. Essentially, the second seal in combination with the first seal allows for a much more controlled and predictable (i.e., lower variation) in moisture ingress so that container moisture budgets can be much more precisely met. This allows for a reduction in desiccant material necessary per vial and hence a reduction in production costs associated with the reduced amount of desiccant material.

Example 2

Tests were run to measure moisture ingress of 17 ml vials according to the container embodiment shown in FIGS. 6-10B (Group A'). Ambient conditions were set at 30° C. and 70% relative humidity. There were 144 such containers in the tested population. These moisture ingress results were compared against testing data gathered from testing a population of 2923 containers (Group B') that were identical in material respects to the containers of Group A', except the containers of Sample B' only included the first seal (plastic-to-plastic)—not the second seal (elastomer-to-plastic). The following table shows a side-by-side comparison of the data collected.

| Sample | Mean Ingress (μg/day) | Standard Deviation (μg/day) | Sample Size |
| --- | --- | --- | --- |
| A' | 305.4 | 20.54 | 144 |
| B' | 420.7 | 76.91 | 2923 |

As with Example 1, the data show that addition of the second seal resulted in a meaningful reduction of the mean ingress and a surprisingly significant reduction in the standard deviation of moisture ingress.

While the invention has been described in detail and with reference to specific examples thereof, it will be apparent to one skilled in the art that various changes and modifications can be made therein without departing from the spirit and scope thereof.

What is claimed is:

1. A moisture tight container comprising:
a body defining an interior configured for housing product, and an opening leading to the interior;
a lid that is connected to the body by a hinge, the lid being movable with respect to the body between a closed position in which the lid covers the opening and is mated to the body, and an opened position in which the lid is not mated to the body;
a plurality of seals between the body and the lid and in series when the lid is in the closed position, the plurality of seals including at least a first seal requiring an opening force to transition from the closed position to the opened position, and a second seal in combination with the first seal not requiring more than the opening force to transition from the closed position to the opened position, the first seal being formed by mating incompressible thermoplastic-to-thermoplastic sealing surfaces, the first seal including an undercut of the body relative to a central axis of the body, the second seal being formed by mating elastomer-to-thermoplastic sealing surfaces, wherein the elastomer-to-thermoplastic sealing surfaces include an elastomer, that is compressible and resilient, formed in the lid or on the body,
wherein a combination of the first and second seals in series reduces a moisture vapor ingress of the container while maintaining the opening force in a range that is ergonomically advantageous to a consumer,
wherein the elastomer is injection molded with the body and lid in a multi-shot injection molding process,
wherein the opening force is from 3 to 7 lbf (pound-force).

2. The container according to claim 1, wherein the container when the lid is in the closed position has a moisture vapor transmission rate (MVTR) of less than 370 μg/day at 30° C. and 80% RH.

3. The container of claim 2, wherein the elastomer is made from a thermoplastic elastomer (TPE).

4. The container of claim 3, wherein at least one of the thermoplastic-to-thermoplastic sealing surfaces is on a radially-projecting rim along an outside of the body.

5. The container of claim 3, wherein at least one of the elastomer-to-thermoplastic sealing surfaces is on a radially-projecting rim along an outside of the body.

6. A moisture tight container comprising:
a container body having a base and a sidewall extending therefrom, the body defining an interior configured for housing product, the sidewall terminating at a lip having a top edge, the lip surrounding an opening leading to the interior; and
a lid movable with respect to the container body between a closed position in which the lid covers the opening to create a moisture tight seal with the body and an open position in which the opening is exposed, the moisture tight seal comprising a plurality of seals between the body and the lid when the lid is in the closed position, the plurality of seals including at least a first seal and a second seal, the first seal being formed by mating a thermoplastic sealing surface of the body to a thermoplastic sealing surface of the lid, the second seal being formed by mating a thermoplastic sealing surface of the body with an elastomeric sealing surface of the lid, the elastomeric sealing surface being an elastomeric ring made from a thermoplastic elastomer (TPE), a first portion of the elastomeric ring being compressed by the top edge of the lip when the lid is in the closed position and a second portion of the elastomeric ring maintaining an original, uncompressed shape when the lid is in the closed position thereby creating an indentation along an engagement surface of the elastomeric ring between the first portion and the second portion.

7. The container of claim 6, wherein the first seal requires an opening force to transition from the closed position to the opened position and the second seal in combination with the first seal does not require more than the opening force to transition from the closed position to the opened position.

8. A moisture tight container comprising,
a container body having a base and a sidewall extending therefrom, the body defining an interior configured for housing product, the sidewall terminating at a lip having a top edge, the lip surrounding an opening leading to the interior; and
a lid movable with respect to the container body between a closed position in which the lid covers the opening to create a moisture tight seal with the body and an open position in which the opening is exposed, the moisture tight seal comprising a plurality of seals between the body and the lid when the lid is in the closed position, the plurality of seals including at least a first seal and a second seal, the first seal being formed by mating a thermoplastic sealing surface of the body to a thermoplastic sealing surface of the lid, the second seal being formed by mating a thermoplastic sealing surface of the body with an elastomeric sealing surface of the lid, the elastomeric sealing surface being an elastomeric ring made from a thermoplastic elastomer (TPE), a first portion of the elastomeric ring being compressed by the top edge of the lip when the lid is in the closed position, a second portion of the elastomeric ring maintaining an original, uncompressed shape when the lid is in the closed position, wherein the first seal requires an opening force to transition from the closed position to the opened position and the second seal in combination with the first seal does not require more than the opening force to transition from the closed position to the opened position, and wherein the opening force is from 3 to 7 lbf (pound-force).

9. A moisture-tight container comprising, a container body having a base and a sidewall extending therefrom, the body defining an interior configured for housing product, the sidewall terminating at a lip having a top edge, the lip surrounding an opening leading to the interior; and a lid movable with respect to the container body between a closed position in which the lid covers the opening to create a moisture tight seal with the body and an open position in which the opening is exposed, the moisture tight seal comprising a plurality of seals between the body and the lid when the lid is in the closed position, the plurality of seals including at least a first seal and a second seal, the first seal being formed by mating a thermoplastic sealing surface of the body to a thermoplastic sealing surface of the lid, the second seal being formed by mating a thermoplastic sealing surface of the body with an elastomeric sealing surface of the lid, the elastomeric sealing surface being an elastomeric ring made from a thermoplastic elastomer (TPE), a first portion of the elastomeric ring being compressed by the top edge of the lip when the lid is in the closed position, a second portion of the elastomeric ring maintaining an original, uncompressed shape when the lid is in the closed position, wherein the elastomeric ring has a Shore A hardness from 20 to 50 and a thickness from 0.25 mm to 1.25 mm.

10. A moisture-tight container comprising, a container body having a base and a sidewall extending therefrom, the body defining an interior configured for housing product, the sidewall terminating at a lip having a top edge, the lip surrounding an opening leading to the interior; and a lid movable with respect to the container body between a closed position in which the lid covers the opening to create a moisture tight seal with the body and an open position in which the opening is exposed, the moisture tight seal comprising a plurality of seals between the body and the lid when the lid is in the closed position, the plurality of seals including at least a first seal and a second seal, the first seal being formed by mating a thermoplastic sealing surface of the body to a thermoplastic sealing surface of the lid, the second seal being formed by mating a thermoplastic sealing surface of the body with an elastomeric sealing surface of the lid, the elastomeric sealing surface being an elastomeric ring made from a thermoplastic elastomer (TPE), a first portion of the elastomeric ring being compressed by the top edge of the lip when the lid is in the closed position, a second portion of the elastomeric ring maintaining an original, uncompressed shape when the lid is in the closed position, wherein the container, when the lid is in the closed position, has a moisture vapor transmission rate (MVTR) of less than 400 µg/day at 30° C. and 80% RH.

11. The container of claim 6, wherein the elastomeric ring is injection molded with the container body and lid in a multi-shot injection molding process.

12. The container of claim 6, wherein the first seal includes an undercut of the body relative to a central axis of the body.

13. The container of claim 12, wherein the lid includes a depending skirt, and wherein the undercut has a surface that mates with a corresponding surface of the skirt thereby forming the first seal.

14. The container of claim 6, wherein the first seal and the second seal combined provide the container when the lid is in the closed position a lower moisture vapor transmission rate (MVTR) than the first seal would provide without the second seal.

15. The container of claim 6, further comprising a plurality of test strips stored therein.

16. A moisture tight container, comprising:

a body having a base and a sidewall extending upwardly therefrom, the sidewall terminating at a lip opposite the base, the body defining an interior configured for housing product, the body further having an opening leading to the interior, the opening being surrounded by the lip, a rim projecting radially outwardly from the sidewall below the opening;

a lid having a base and a skirt depending therefrom, the lid being connected to the body by a living hinge, the hinge being attached to the rim of the body, the lid being pivotable about the hinge with respect to the container body to move the container between a closed position in which the lid covers the opening so as to create a moisture tight seal with the body and an open position in which the opening is exposed, the moisture tight seal comprising at least a first seal and a second seal, wherein the first seal is formed by mating a thermoplastic sealing surface of the body to a thermoplastic sealing surface of the lid, the first seal is formed between an undercut of the body relative to a central axis of the body and an undercut surface of the lid, the second seal being formed by mating a thermoplastic sealing surface of the body with an elastomeric sealing surface of the lid, the elastomeric sealing surface comprising an elastomeric ring attached to an interior surface of the base of the lid, the elastomeric ring being compressed by an upper surface of the lip surrounding the opening when the lid is in the closed position, the elastomeric ring vertically compressing when the lid is in the closed position, wherein the container, when the lid is in the closed position, has a moisture vapor transmission rate (MVTR) of less than 400 µg/day at 30° C. and 80% RH, and wherein the elastomeric sealing surface comprises an elastomeric ring having a Shore A hardness from 20 to 50 and a thickness from 0.25 mm to 1.25 mm, and wherein an interior surface of the base of the lid is spaced apart from a top surface of the lip when the lid is in the closed position.

17. The container of claim 16, wherein vertical compression of the elastomeric ring causes a portion of the ring to elastically expand radially.

18. The container of claim 17, wherein the portion of the ring elastically expands radially into a void provided between the body and the lid.

19. The container of claim 18, further comprising an elastomeric sealing surface attached to an interior surface of the lid base, wherein the moisture tight seal further includes a second elastomeric-to-thermoplastic seal created by mating the elastomeric sealing surface and a lip of the container body, the lip surrounding the opening of the container body.

20. A moisture-tight container comprising,
a container body having a base and a sidewall extending therefrom, the body defining an interior configured for housing product, the sidewall terminating at a lip having a top edge, the lip surrounding an opening leading to the interior; and
a lid movable with respect to the container body between a closed position in which the lid covers the opening to create a moisture tight seal with the body and an open position in which the opening is exposed, the moisture tight seal comprising a plurality of seals between the body and the lid when the lid is in the closed position, the plurality of seals including at least a first seal and a second seal, the first seal being formed by mating a thermoplastic sealing surface of the body to a thermoplastic sealing surface of the lid, the second seal being formed by mating a thermoplastic sealing surface of the body with an elastomeric sealing surface of the lid, the elastomeric sealing surface being an elastomeric ring made from a thermoplastic elastomer (TPE), a first portion of the elastomeric ring being compressed by the top edge of the lip when the lid is in the closed position, a second portion of the elastomeric ring maintaining an original, uncompressed shape when the lid is in the closed position,
wherein the top edge of the lip is planar and devoid of an annular recess.

21. A moisture-tight container comprising,
a body having a base and a sidewall extending upwardly therefrom, the sidewall terminating at a lip opposite the base, the body defining an interior configured for housing product, the body further having an opening leading to the interior, the opening being surrounded by the lip, a rim projecting radially outwardly from the sidewall below the opening;
a lid having a base and a skirt depending therefrom, the lid being connected to the body by a living hinge, the hinge being attached to the rim of the body, the lid being pivotable about the hinge with respect to the container body to move the container between a closed position in which the lid covers the opening so as to create a moisture tight seal with the body and an open position in which the opening is exposed, the moisture tight seal comprising at least a first seal and a second seal,
wherein the first seal is formed by mating a thermoplastic sealing surface of the body to a thermoplastic sealing surface of the lid, the first seal is formed between an undercut of the body relative to a central axis of the body and an undercut surface of the lid, the second seal being formed by mating a thermoplastic sealing surface of the body with an elastomeric sealing surface of the lid, the elastomeric sealing surface comprising an elastomeric ring attached to an interior surface of the base of the lid, the elastomeric ring being compressed by an upper surface of the lip surrounding the opening when the lid is in the closed position, the elastomeric ring vertically compressing when the lid is in the closed position,
wherein the container, when the lid is in the closed position, has a moisture vapor transmission rate (MVTR) of less than 400 µg/day at 30° C. and 80% RH, and wherein the elastomeric sealing surface comprises an elastomeric ring having a Shore A hardness from 20 to 50 and a thickness from 0.25 mm to 1.25 mm, and
wherein the top edge of the lip is planar and devoid of an annular recess.

* * * * *

UNITED STATES PATENT AND TRADEMARK OFFICE
CERTIFICATE OF CORRECTION

PATENT NO. : 11,794,959 B2
APPLICATION NO. : 17/454649
DATED : October 24, 2023
INVENTOR(S) : Jonathan R. Freedman et al.

It is certified that error appears in the above-identified patent and that said Letters Patent is hereby corrected as shown below:

In the Claims

Column 18, Claim 21, Lines 31-33, replace "and wherein the elastomeric sealing surface comprises an elastomeric ring having a Shore A hardness from 20 to 50 and a thickness from 0.25 mm to 1.25 mm," with --and wherein the elastomeric ring has a Shore A hardness from 20 to 50 and a thickness from 0.25 mm to 1.25 mm,--

Signed and Sealed this
Twelfth Day of March, 2024

Katherine Kelly Vidal
*Director of the United States Patent and Trademark Office*